(12) United States Patent
Rosenberg et al.

(10) Patent No.: US 9,713,662 B2
(45) Date of Patent: Jul. 25, 2017

(54) SMART TIP LVAD INLET CANNULA

(71) Applicant: The Penn State Research Foundation, University Park, PA (US)

(72) Inventors: Gerson Rosenberg, Lebanon, PA (US); Joshua P. Cysyk, Hershey, PA (US); William J. Weiss, Mechanicsburg, PA (US); Raymond K. Newswanger, Terre Hill, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 14/648,320

(22) PCT Filed: Dec. 2, 2013

(86) PCT No.: PCT/US2013/072611
§ 371 (c)(1),
(2) Date: May 29, 2015

(87) PCT Pub. No.: WO2014/085806
PCT Pub. Date: Jun. 5, 2014

(65) Prior Publication Data
US 2015/0306290 A1    Oct. 29, 2015

Related U.S. Application Data

(60) Provisional application No. 61/731,879, filed on Nov. 30, 2012.

(51) Int. Cl.
*A61M 1/10* (2006.01)
*A61B 5/00* (2006.01)
(Continued)

(52) U.S. Cl.
CPC ......... *A61M 1/1008* (2014.02); *A61B 5/0215* (2013.01); *A61B 5/0538* (2013.01);
(Continued)

(58) Field of Classification Search
USPC ...................................... 600/17–18
See application file for complete search history.

(56) References Cited

U.S. PATENT DOCUMENTS

| 6,716,157 B2 | 4/2004 | Goldowsky |
| 2004/0152944 A1 | 8/2004 | Medvedev et al. |

(Continued)

OTHER PUBLICATIONS

International Preliminary Report on Patentability and Written Opinion of the International Searching Authority for PCT/US2013/072611 mailed Jun. 11, 2015.
(Continued)

*Primary Examiner* — Nicole F Johnson
(74) *Attorney, Agent, or Firm* — Buchanan Ingersoll & Rooney PC

(57) ABSTRACT

Embodiments of the invention provide a left ventricular assist device (LVAD) cannula that includes multiple independent sensors may help decrease the incidence of ventricular collapse and provide automatic speed control. A cannula may include two or more independent sensors. One sensor may measure ventricular pressure, while another may measure ventricular volume and/or ventricular wall location. With this information an automatic control system may be configured to adjust pump speed to minimize the likelihood of ventricular collapse and maximize LVAD flow in response to physiologic demand. Typically the volume sensors are conductance sensors. Further embodiments provide LVADs that are powered by RF energy.

20 Claims, 12 Drawing Sheets

(51) Int. Cl.
   *A61B 5/0215* (2006.01)
   *A61B 5/053* (2006.01)
   *A61M 1/12* (2006.01)

(52) U.S. Cl.
   CPC ......... *A61B 5/6869* (2013.01); *A61M 1/1086* (2013.01); *A61M 1/122* (2014.02); *A61M 1/127* (2013.01); *A61M 2205/3303* (2013.01); *A61M 2205/3317* (2013.01); *A61M 2205/3334* (2013.01); *A61M 2205/3344* (2013.01); *A61M 2205/3523* (2013.01); *A61M 2230/04* (2013.01)

(56) References Cited

U.S. PATENT DOCUMENTS

2005/0159639 A1   7/2005   Skliar et al.
2007/0156006 A1   7/2007   Smith et al.
2009/0203957 A1*  8/2009   LaRose ................. A61M 1/101
                                                          600/18
2011/0071588 A1   3/2011   Ding et al.
2013/0066141 A1*  3/2013   Doerr ................... A61N 1/3627
                                                          600/17

OTHER PUBLICATIONS

Hendry et al., "The HeartSaver Left Ventricular Assist Device: An Update", The Annuals of Thoracic Surgery, 2001, 166-170, vol. 71, The Society of Thoracic Surgeons.

Goldstein et al., "Noncardiac Surgery in Long-Term Implantable Left Ventricular Assist-Device Recipients", Annuals of Surgery, 1995, 203-207, vol. 222, No. 2, Lippincott-Raven Publishers.

Baan et al., "Continuous Measurement of Left Ventricular Volume in Animals and Humans by Conductance Catheter", Journal of the American Heart Association, 1984, 812-823, vol. 70, No. 5, http://circ.ahajournals.org.

Valgimigli, "High-Risk Percutaneous Intervention in the Drug-Eluting Stent Era", Thesis, 1-225.

PCT/US2013/072611 International Search Report and Written Opinion dated Apr. 24, 2014.

* cited by examiner

SMART TIP LVAD INLET CANNULA

CROSS-REFERENCE TO RELATED APPLICATIONS

This application is the national phase under 35 U.S.C. §371 of PCT International Application No. PCT/US2013/072611, filed on Dec. 2, 2013, which claims priority to U.S. Provisional Patent App. No. 61/731,879, filed on Nov. 30, 2012, and which is incorporated by reference herein.

STATEMENT REGARDING FEDERALLY SPONSORED RESEARCH OR DEVELOPMENT

This invention was made with government support under Grant No. HL081119, awarded by the National Institutes of Health. The Government has certain rights in the invention.

BACKGROUND OF THE INVENTION

Field of the Invention

Embodiments of the invention relate to continuous-flow left ventricular assist devices (LVADs) and methods for their use.

Description of the Related Art

A left ventricular assist device or "LVAD" is a mechanical device that is typically placed in the chest or abdomen of a patient to assist with pumping blood in the patient's body. The LVAD is usually affixed so that it pumps blood from the left ventricle to the aorta of the patient. Normally an LVAD will include a cable that passes through the skin of a patient to allow control and assessment of the LVAD. The cable also allows connection to a controller, power pack, and, typically, a reserve power pack.

Long-term mechanical circulatory support is being used more frequently as bridge-to-transplantation and destination therapy for heart failure patients because of improved safety and reliability of left ventricular assist devices. In addition, mechanically unloading the ventricle reduces wall stress and myocardial oxygen consumption. This can lead to reverse modeling of the myocardium and recovery from heart failure in some instances. Recently, the use of continuous flow assist devices has become common due to their small size and valve-less design.

Unlike pulsatile LVADs, in which pump filling and ejection are determined in part by the patient's physiology and inlet cannula suction pressure is limited by atmospheric pressure, continuous flow LVADs produce a flow-dependent differential pressure as a function of pump speed as described by the characteristic pressure versus flow (H-Q) curve. If the speed is too slow, the patient may not receive an optimal amount of blood flow and their activities may still be limited by their heart failure. If the pump speed is too fast, the pump can empty the ventricle, pulling the ventricular wall towards the pump inlet and subsequently limiting flow. This phenomenon, referred to as a suction event, can cause myocardial damage and dangerous ventricular arrhythmias.

Infrequent but occasional aortic valve opening is often used as a guideline to set pump speed, indicating the ventricle has adequate residual volume at end-systole to prevent suction and is unloaded to some extent. However, the aortic valve opening is only measured in the clinic setting and is subject to changes in left ventricular (LV) contractility, heart rate, arterial pressure, and blood volume related to normal daily activities (e.g. sleep, exercise, positional changes, etc.). An automatic control algorithm is desirable to adjust pump speed in response to hemodynamic changes in order to provide sufficient support but reduce the risk of suction-induced arrhythmogenesis.

Of the many methods that have been devised to control continuous flow LVADs, most rely on an estimate of instantaneous pump flow based on the motor equation and power dissipation. However, accuracy is affected by the blood viscosity, model non-linearities, and noise in the power measurement. In addition, pump flow alone cannot determine the ventricular workload, and therefore, cannot be used to optimize pump speed to unload the ventricle. A control algorithm based on direct measurement of left ventricular volume and/or left ventricular pressure would be advantageous in preventing suction events and setting an optimal operating point that reflects ventricular loading. Once established, this control system can be used with existing pumps used clinically and allow adaptive flow control that can adjust with physiologic demand (i.e. changes in ventricular load). As LVAD patients leave the hospital and return to their daily activities, the control system will be able to adapt to the patient's circulatory needs and prevent adverse suction events.

BRIEF SUMMARY OF THE INVENTION

We have found that an LVAD that includes independent sensors for measuring at least one of ventricular pressure and volume may help decrease the incidence of ventricular collapse. We refer to this as a "smart" inlet cannula with integrated sensors for measuring pressure and/or volume of the left ventricle ("LV"). An automatic control system can use the volume and pressure information to adjust pump speed to minimize the likelihood of collapse. In addition, the control system can use the sensor information to assess circulatory needs (e.g. during exercise), and adjust pump speed accordingly. The sensors are conductance electrodes for measuring volume and a pressure sensor. Further embodiments provide LVADs that are powered by RF energy.

DETAILED DESCRIPTION OF THE FIGURES

Figure 4:
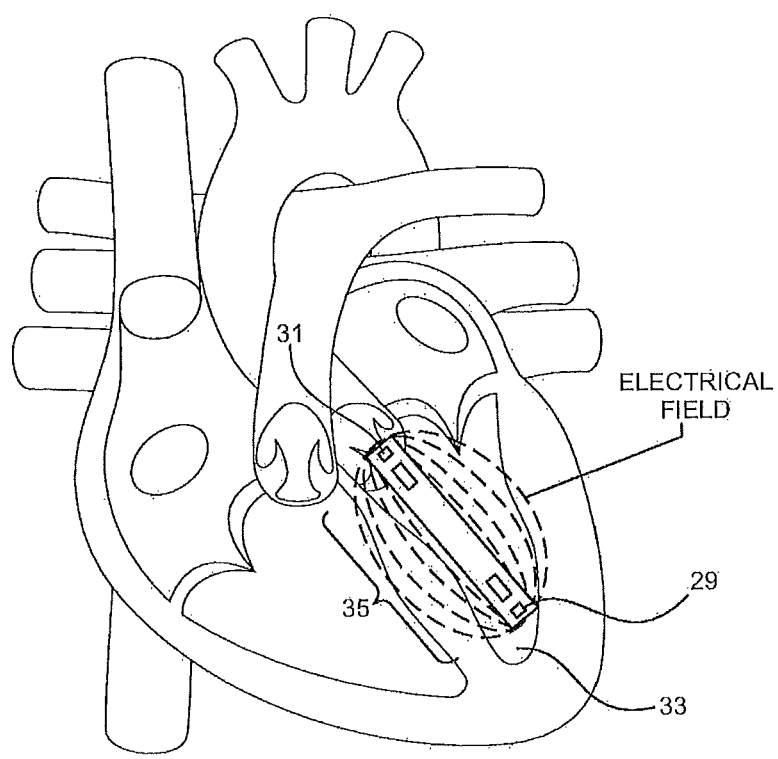

FIG. 4 details electrodes of a conventional conductance catheter.

Figure 5:
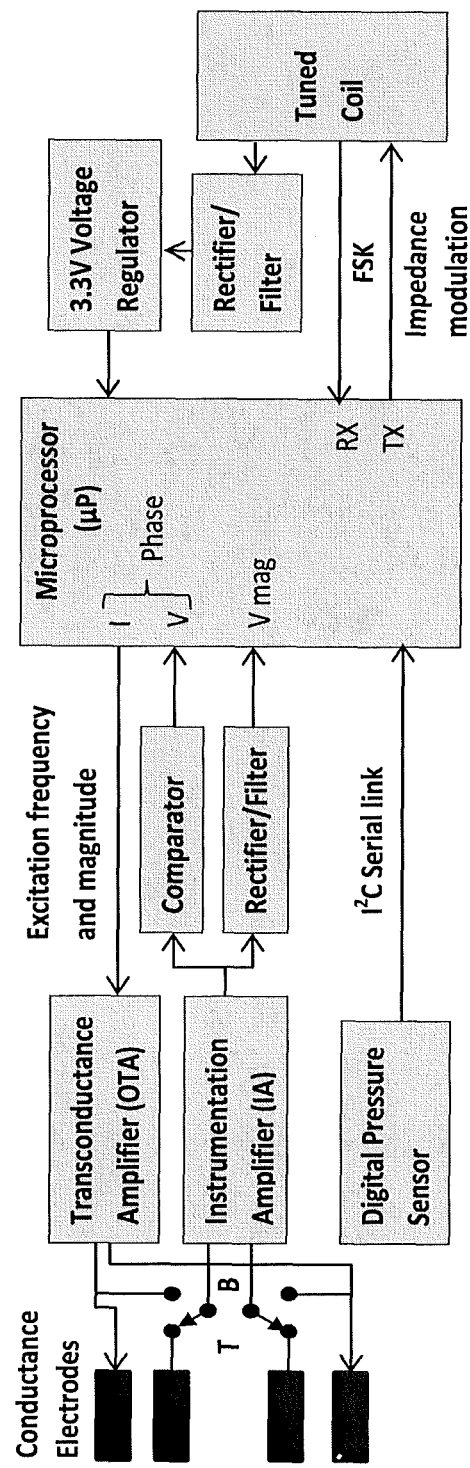

FIG. 5 shows a block diagram of the smart tip internal electronics.

Figure 6:
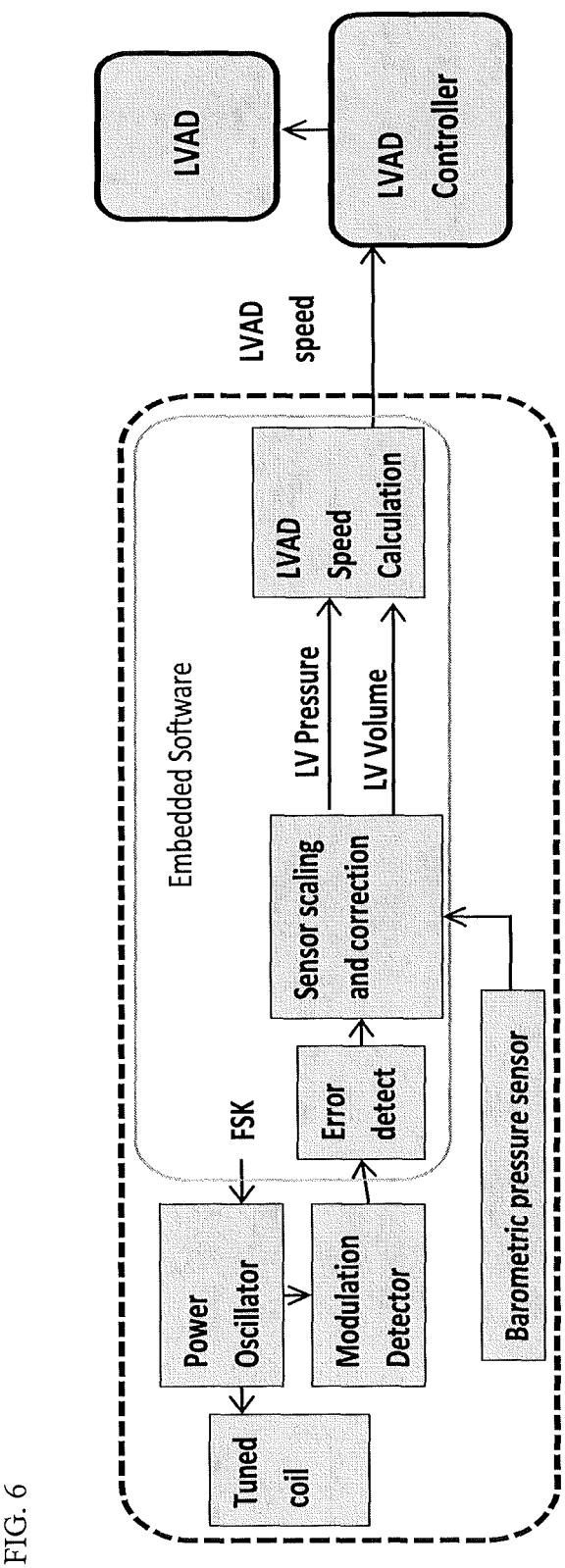

FIG. 6 shows a block diagram of the external transceiver.

Figure 7:
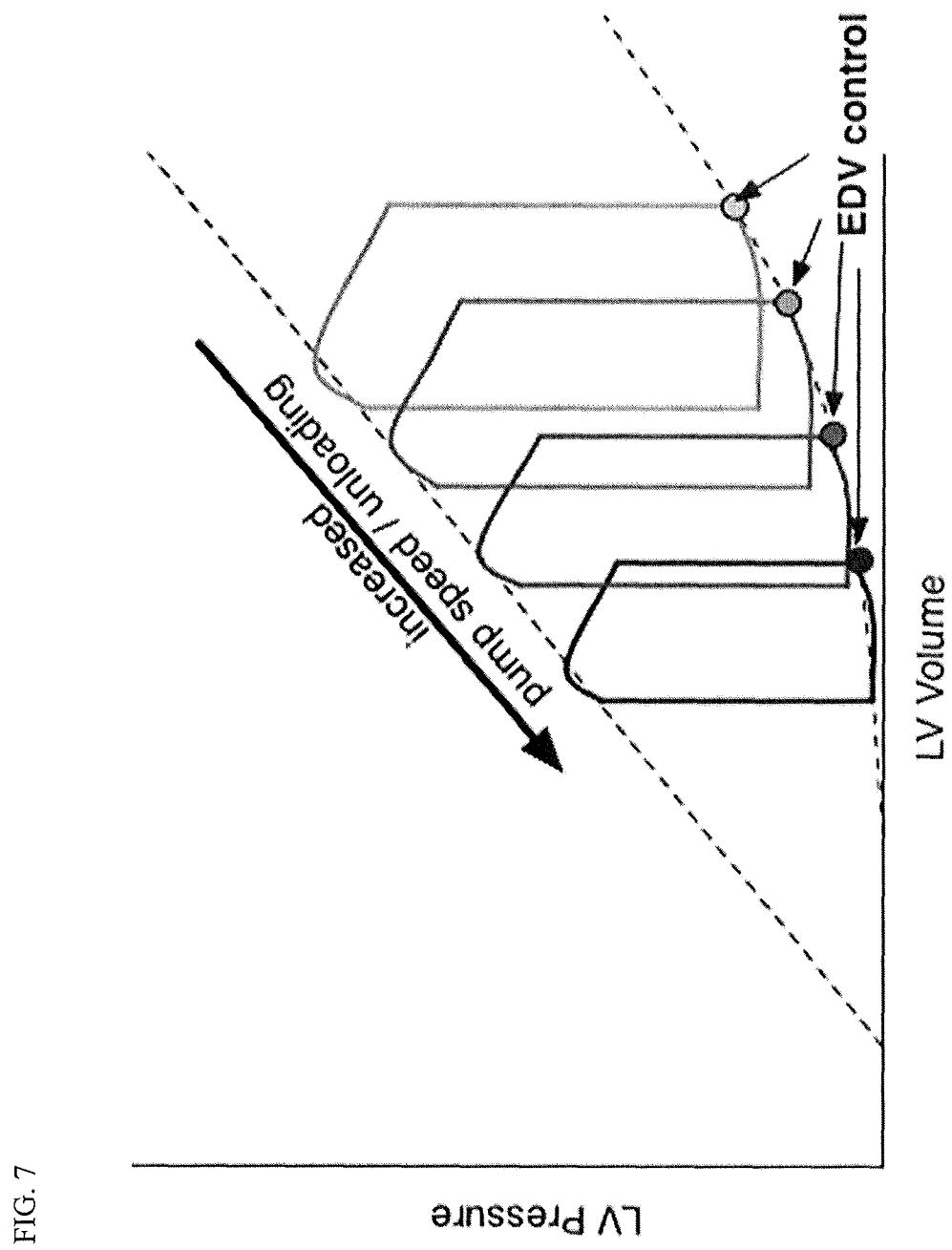

FIG. 7 shows left ventricular pressure-volume relationship as a function of LVAD pump speed.

Figure 8:
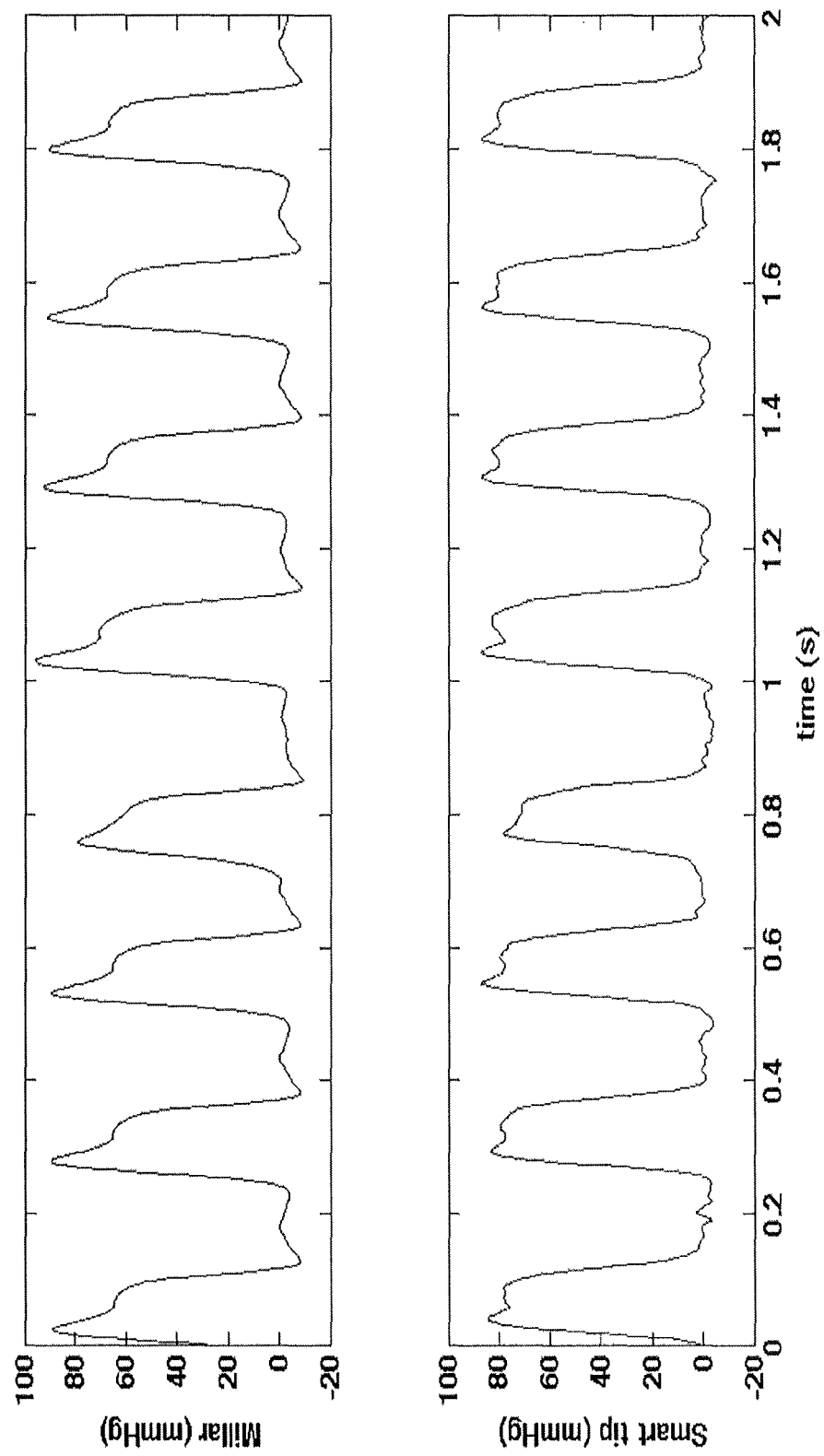

FIG. 8 shows signals recorded from the smart tip pressure sensor compared to a reference Millar transducer during an acute ovine study.

Figure 9:
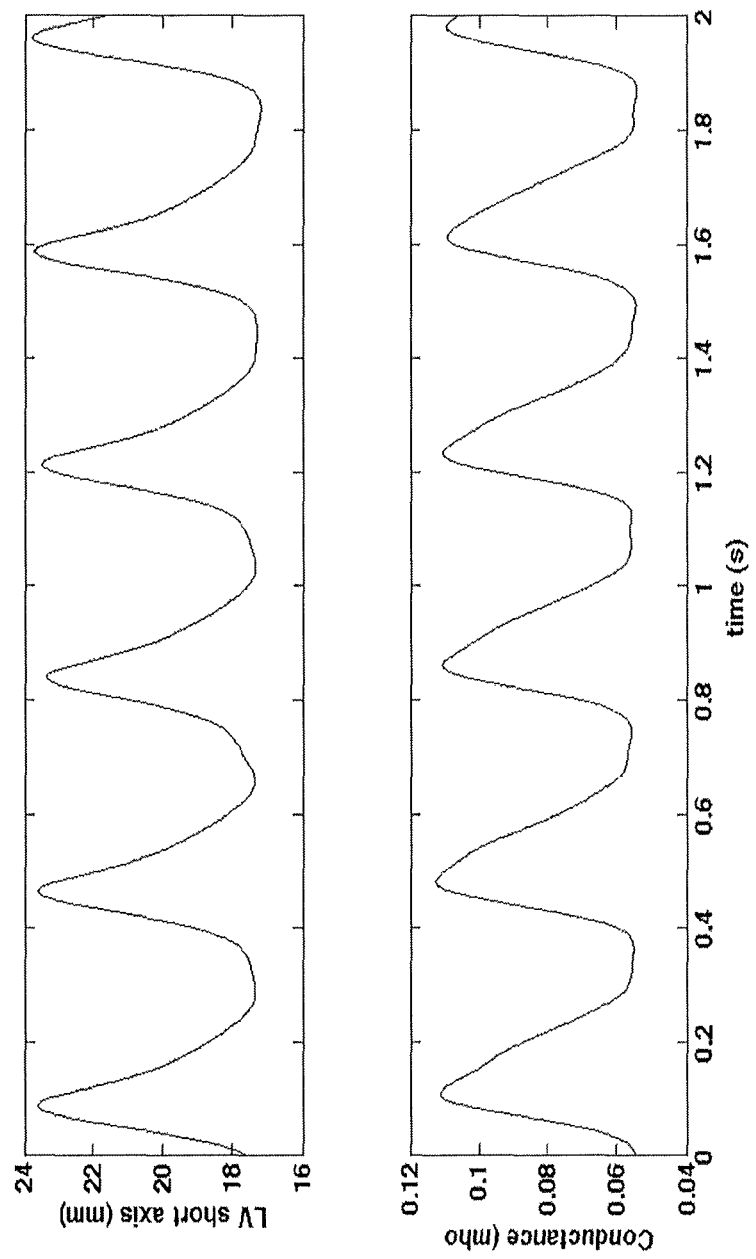

FIG. 9 shows signals recorded from the smart tip volume sensor compared to the LV short axis dimension measured using sonomicrometry during an acute ovine study.

Figure 10:
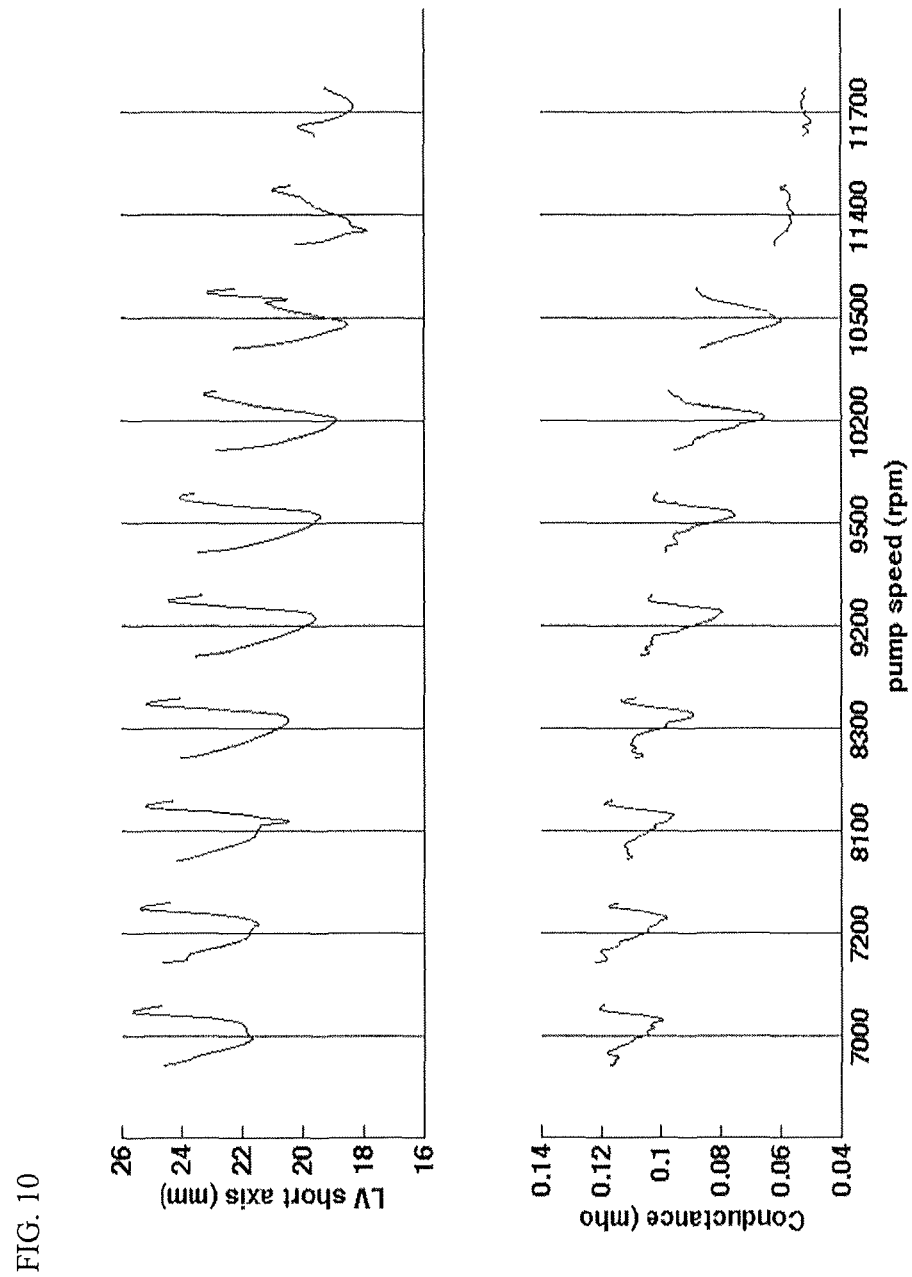

FIG. 10 shows signals recorded from the smart tip conductance sensor compared with the LV short axis dimension as pump speed increased leading to suction during an acute ovine study.

Figure 11:
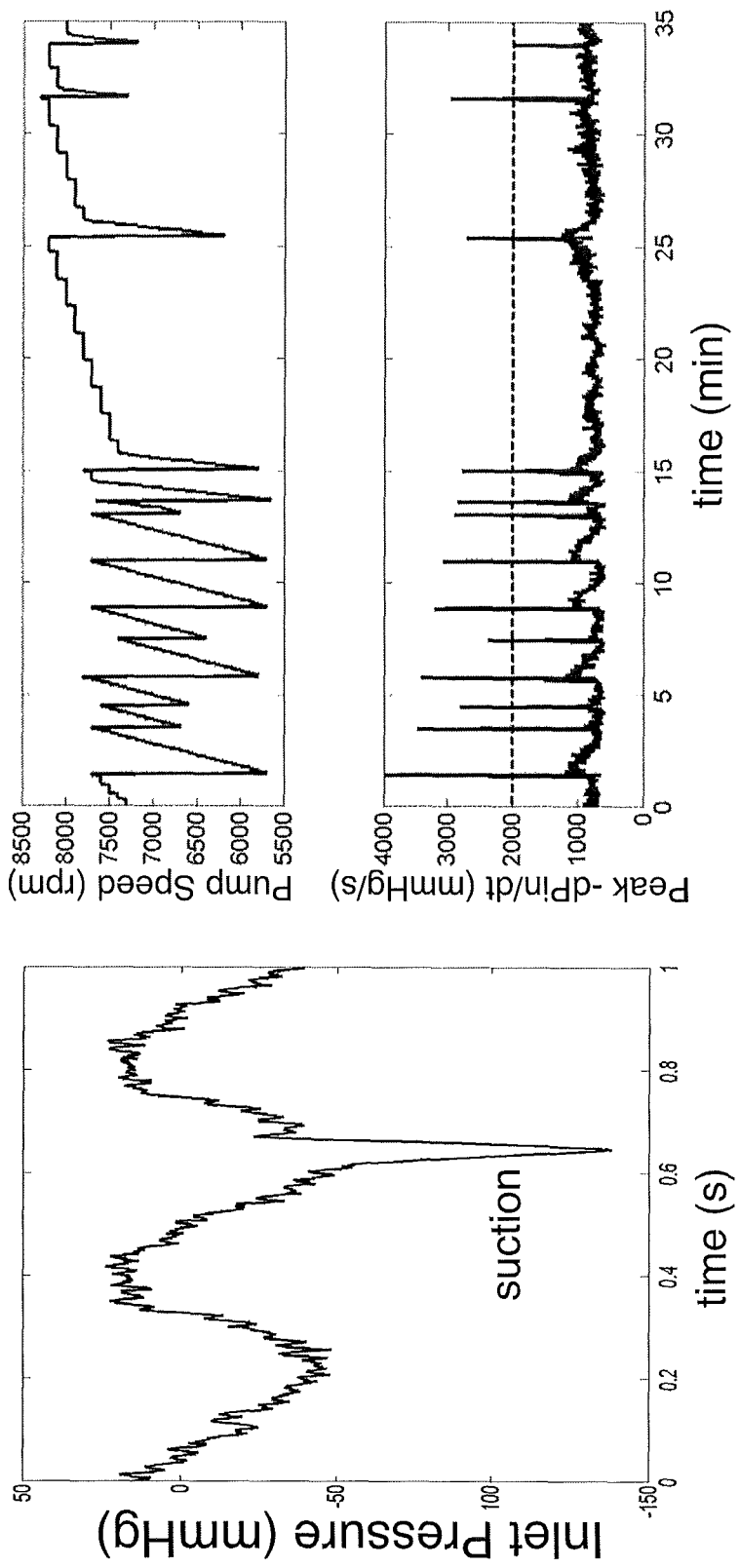

FIG. 11 shows an example of suction detection based on inlet pressure in an acute calf study.

Figure 12:
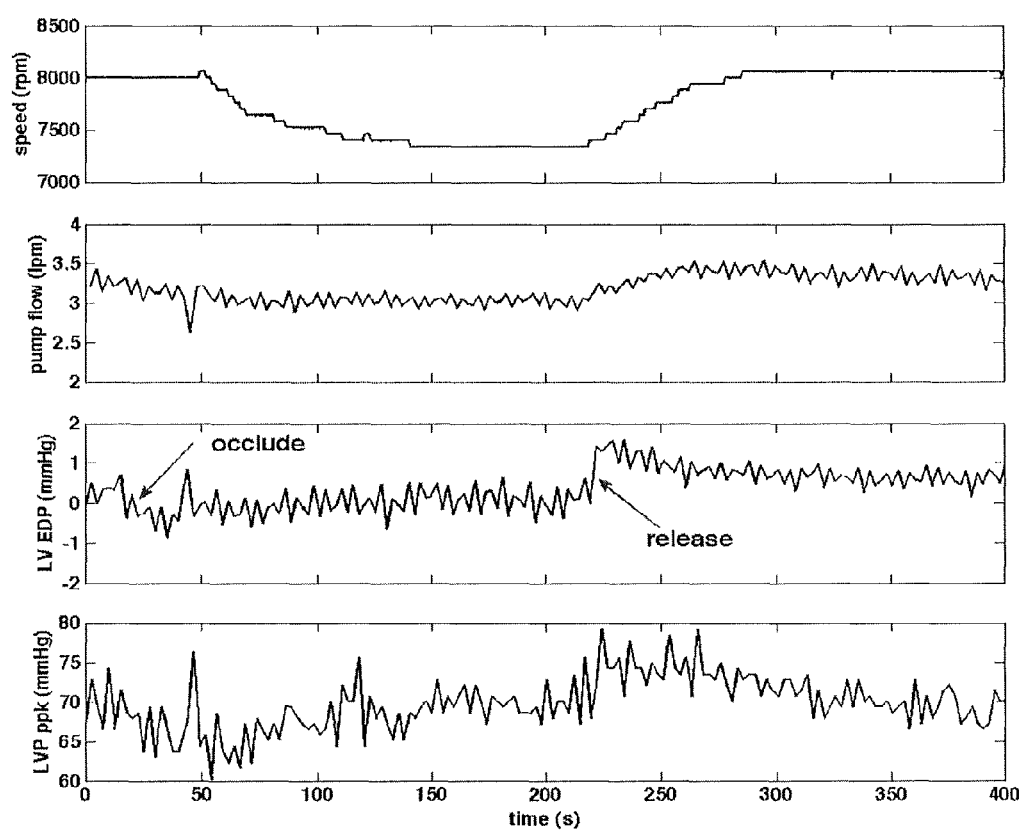

FIG. 12 shows and example of LV unloading control based on inlet pressure in an acute ovine study.

DETAILED DESCRIPTION OF THE INVENTION

We have found that a left-ventricular assist device ("LVAD") that includes multiple independent sensors may help decrease the incidence of ventricular collapse during LVAD use. Embodiments of the invention may include conductance electrodes and/or pressure sensors in an LVAD cannula tip for determination of ventricular pressure, ventricular volume, and ventricular wall location.

Figure 1:
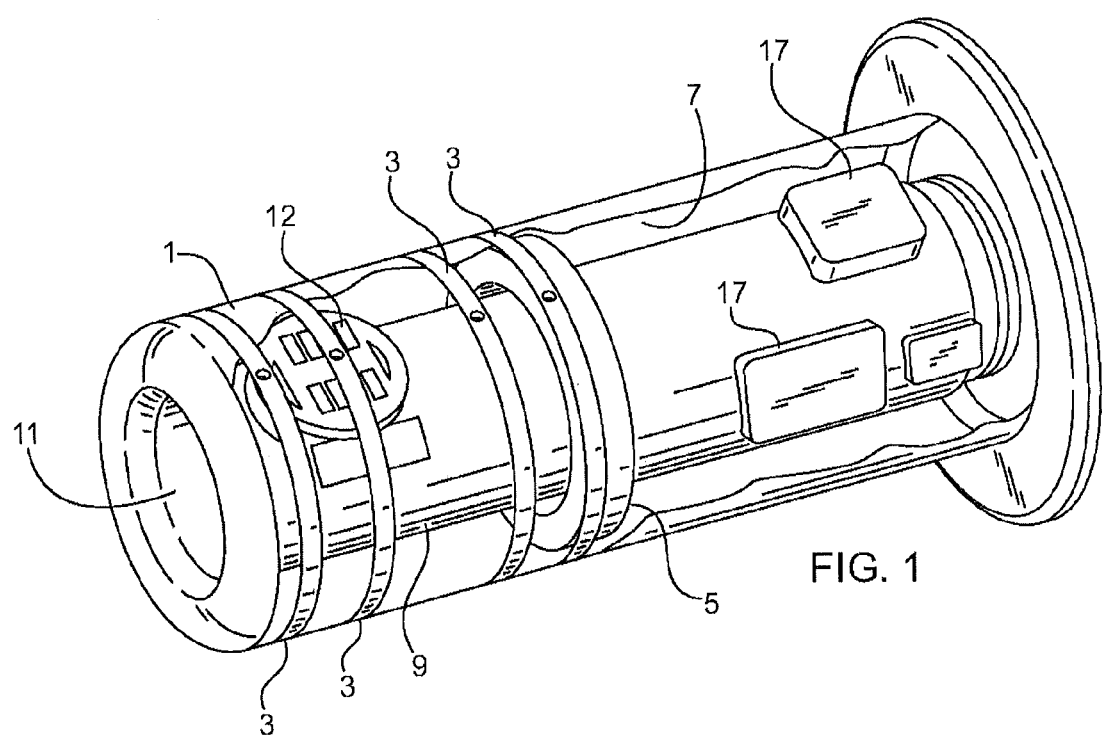
FIG. 1 shows an engineering design of an embodiment of the invention.

The sensors are conductance and/or pressure sensors. The use of conductance electrode technology may be better understood with reference to the figures. FIG. 1 shows an embodiment of the invention in which a wall is shown as transparent. This transparency is for the convenience of the viewer in FIG. 1, and is not a requirement of embodiments of the invention. FIG. 1 shows an LVAD cannula tip including an outer wall 1 surrounded by a plurality of concentric electrodes 3 in communication with electronics 17 and a transceiver coil 5. In a preferred embodiment there are four concentric platinum electrodes, though those of skill in the art will, with the benefit of this disclosure, recognize that additional numbers and types of electrodes are possible. For example, electrodes may be made from titanium with a thin layer of platinum black on the blood contacting surface.

The transceiver coil is located in a cavity 7 defined by an inner wall 9 and the outer wall. The inner wall also defines an opening 11 for the LVAD inlet cannula. A pressure transducer 12 is mounted between the inner and outer walls, with the sensing surface in communication with a small sensing chamber filled with silicone gel. One side of this chamber is formed by the inner wall where the wall thickness is very thin, such that blood pressure on the inner wall is transmitted to the sensing chamber and thereby to the pressure sensor. The cannula tip is connected to a cannula (a flexible tube that carries blood) which then connects to the LVAD inlet port. In another embodiment the cannula tip may be incorporated directly in to the LVAD inlet port, such that a cannula is not used.

In a preferred embodiment, the pressure sensor communicates with electronics that provide functions such as signal conditioning, excitation, and analog-to-digital conversion or other processing. A transceiver coil enables wireless transmission of data to an external receiver and LVAD controller, and also functions as a receiver for wireless power coupled inductively from a power transmitting coil placed outside the body. Separate coils may also be used for receiving power, receiving data, and transmitting data. Electronics may also provide functions related to power reception and conditioning. Electronics may also be located in a separate location, or a portion of the electronics may be located in the tip, and power and data may be transmitted over cables.

In a typical embodiment of the device, four electrodes are used for conductance measurements. In this arrangement a time-varying current source is applied through the outer electrode pair, and voltage is measured across the inner pair of electrodes. Separating the measurement electrodes from the source electrodes eliminates measurement errors due to the polarization potential at the electrode-blood interface.

The conductance that is measured when the LVAD cannula is used will be a combination of the conductance of the blood (the desired blood volume measurement) and the surrounding tissue. The conductance of the surrounding tissue may be compensated for by a dual frequency method or by the methods of Baan et al or Wei et al. Determination of conductance is also reported in more detail herein.

LVADs of embodiments of the invention may include or be connected to an automatic control system. Such a control system may use data obtained through the conductance electrodes and/or pressure sensor to adjust pump speed to minimize the likelihood of ventricular collapse and to maximize pump flow in response to circulatory demand. If the measured volume is below a predetermined threshold, pump speed will be reduced. Likewise, if the measured volume is above a predetermined threshold, pump speed will be increased.

In further embodiments of the invention the LVAD is powered by RF energy. This is accomplished, for example, by inductive coupling between two coils of wire. The internal coil is implanted under the skin and connects to power conditioning circuitry contained in an implantable metal container, similar to a pacemaker. The conditioned power is used to drive the implantable blood pump, and may also recharge implantable batteries to be used whenever power transfer is absent. The external coil is placed against the skin in proximity to (usually within 1 inch of) the internal coil. The external coil is connected to a power oscillator and controller, which produces current in the external coil, and thereby induces current in the internal coil. In most cases the coils are tuned, via capacitors connected in series or parallel with the coils, to resonate at a given frequency which improves power transfer efficiency.

The following information is provided to give a more robust description of various embodiments of the invention, which are described in a feature-by-feature basis. Those skilled in the art will appreciate that these embodiments are exemplary, that they suggest many possible combinations, and that the invention is defined by the claims.

Pressure Sensor Design

The requirements for direct pressure measurements are challenging. The sensing element must be resistant to thrombus formation, which requires non-thrombogenic materials and the absence of crevices, steps, or other surface features. In one embodiment we measure LV pressure relative to atmospheric pressure, as in conventional catheterization P-V loops. For long term VAD implantation, which is now approaching five years in some cases, offset drift should be minimal, although some compensation for drift may be accomplished in a final control algorithm. The frequency response, for control purposes, should be approximately 0-100 Hz.

Pressure Sensor

We have developed a pressure sensor to measure inlet cannula pressure. We have used a pressure signal in a VAD speed controller for avoiding left ventricular suction, both in vivo and in vitro. A strain gage bonded to an area of the pump inlet port that is machined to between 0.001 and 0.005 in thick, for example, provides a signal that is proportional to pressure in the tubing lumen. Finite element modeling (FEA) was used to develop the sensor. This approach provides adequate signal-to-noise ratio, but long term offset drift was suboptimal. This was due to the extremely low strain and the use of individually bonded strain gauge elements directly to a titanium diaphragm. Strain produced by the mismatch in the temperature coefficients of expansion of the silicon, titanium, and adhesive, as well as creep and curing stresses in the adhesive, produced error signals on the same order of magnitude as the pres sure-produced strain of interest. The sensor gain was stable, however, such that control algorithms based on the pulsatility (max-min) of LV pressure would be possible.

Figure 3:
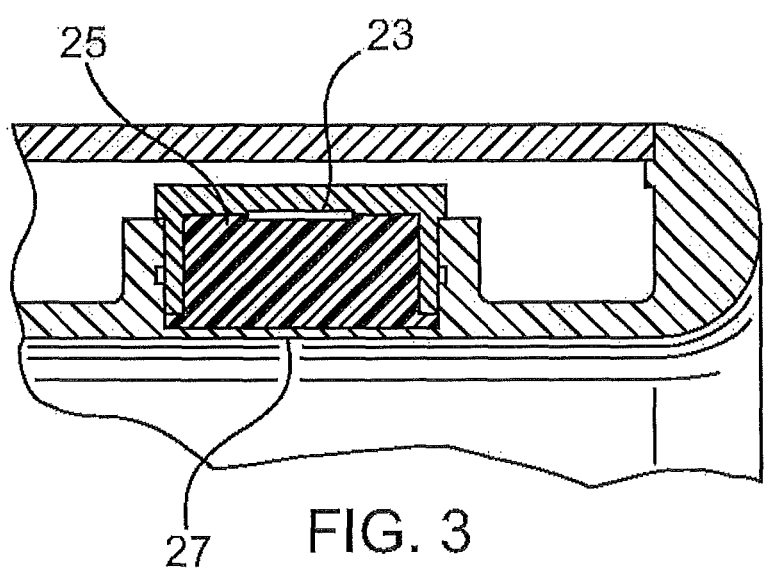
FIG. 3 shows a pressure sensor.

To reduce offset drift described above, we have developed a pressure sensor coupled to a thin-walled section in the inlet cannula lumen. Silicone dielectric gel or silicone oil is used as a couplant between the sensor and the cannula, as shown in FIG. 3. FIG. 3 shows a pressure sensing region 23, silicone gel or oil 25, and a thin wall flexing portion 27 of an inner lumen.

A number of candidate pressure sensors, with similar performance specifications but different mounting options may be suitable for use in embodiments as reported herein. For example, the MS58XX series sensors (Measurement Specialties, Inc., Hampton, Va.) consist of a silicon micromachined pressure sensor die mounted on a 6.2×6.4 mm ceramic carrier or a 6.1×6.3 mm PCB protected by a metal or plastic cap. The sensor element consists of a micromachined silicon membrane with Pyrex glass waferbonded under vacuum to the back side for reference pressure. Ion-implanted resistors make use of the piezoresistive effect to sense pressure applied to the membrane. The sensor is mounted using a process allowing offset stability, making the device suitable for direct PCB assembly. An advantage of this approach is that the offset drift associated with strain gauge bonding is controlled and minimized in the sensor fabrication process. Final assembly of the cannula does not require direct bonding of individual strain gauge elements or die.

Assuming an LV pressure range of −50 to 150 mmHg (gauge), and barometric pressure ranging from normal 1 atm at sea level to the typical aircraft cabin pressure equivalent of 9000 ft elevation, a typical absolute pressure range is given in Table 1.

TABLE 1

Pressure sensor operating range

|  | Gauge Pressure | Absolute Pressure @ sea level (1 atm) | Absolute Pressure @ 9000 ft elevation (0.75 atm) |
|---|---|---|---|
| Minimum | −50 mmHg | 710 mmHg (0.934 atm, 94.7 kPa) | 520 mmHg (0.684 atm, 69.3 kPa) |
| Maximum | 150 mmHg | 910 mmHg (1.197 atm, 121 kPa) | 720 mmHg (0.947 atm, 96.0 kPa) |

Based on specifications of the MS58XX series with maximum pressures in the range of 1 to 1.3 bar absolute, long term offset drift is specified as less than 1 mmHg per year.

Every sensor is individually factory calibrated at two temperatures and two pressures. As a result, 6 coefficients necessary to compensate for process variations and temperature variations are calculated and stored in the 128-bit PROM of each module. These bits (partitioned into 6 coefficients) are read by the microcontroller software and used to provide compensated pressure and temperature values:

C1: Pressure sensitivity
C2: Pressure offset
C3: Temperature coefficient of pressure sensitivity
C4: Temperature coefficient of pressure offset
C5: Reference Temperature
C6: Temperature coefficient of the temperature sensitivity Membrane Strain Estimates The pressure sensor is not in direct contact with blood, but is coupled (via incompressible silicone gel or silicone oil) to a thin-walled section of the cannula lumen, which acts as an isolation diaphragm. Because of the small size and high sensitivity of the MEMS pressure sensing area, the required deflection of the isolation diaphragm is extremely small.

One embodiment of the pressure sensor using the MS5803 sensor and a 0.005 in diaphragm was tested in an acute ovine study. Signals from the smart tip pressure sensor are shown in FIG. 8 compared to a reference sensor implanted in the ventricular cavity (Millar Instruments, Inc.)

Conductance Electrodes

Volume conductance catheters are commonly used in cardiac studies in animals, and occasionally in humans, to provide continuous measures of ventricular volume. Concurrent LV pressure measurements yield P-V loops. As shown in FIG. 4, a pair of constant current conductance electrodes 29 and 31 having excitation and sensing ends create an electric field within a ventricle 33 along a recording segment 35. The electric potential measured at the sensing electrodes is roughly the product of the current density and the total conductance between the electrodes (as well as the uniformity of the electric field).

The original equation for volume by Baan, et al. is $$\text{Volume} = \frac{1}{\alpha}\rho L^2 (G_{meas} - G_p)$$

ρ—blood resistivity
L—length between voltage sensing electrodes
α—a calibration factor
$G_{meas}$—conductance measured
$G_p$—parallel conductance of muscle Gp is measured by using a hypertonic saline bolus method, and the calibration factor α is determined by measuring stroke volume (SV), usually with a flow probe on the aorta in animal studies An improved method developed by Wei et al. uses the complex conductance (i.e. admittance) to separate muscle from blood, since myocardium exhibits both resistance and capacitance, while blood is purely resistive. This improved method reduces errors due to position of the catheter in the ventricle. Wei et al., developed a non-linear equation for volume where γ is a field form factor; this approach demonstrated improved accuracy even with radial misalignment of the catheter. The modified equation for volume is $$\text{Volume} = \frac{1}{1 - G_b/\gamma}\rho L^2 (G_b)$$

$$G_b = |Y|\sin(\theta) - G_m$$

$$G_m = C_m \frac{\sigma_m}{\varepsilon_m}$$

$$C_m = \frac{|Y|\sin(\theta)}{2\pi f}$$

The constants $\sigma_m$ and $\in_m$ are the muscle conductivity and permittivity, respectively. |Y| is the magnitude of the total measured conductance at an excitation frequency f and phase angle θ. In VAD patients, echocardiography, which is routinely performed in VAD patients, will be used to measure end-diastolic and end-systolic admittance in order to compute the field form factor γ, as per Wei et al.

The proposed electrode configuration, in the apical region only, will only be sensitive to blood volume near the cannula tip. However, the total LV volume is expected to be closely related to apical volume, for a given patient, and γ will therefore include correction for the difference between measured apical volume and total volume. Furthermore, for the suction avoidance control, the volume near the cannula tip is more relevant than total volume.

An advantage in this application is the large diameter of the inlet cannula, compared to the small diameter of conductance catheters; the increased electrode surface area will provide reduced electrode impedance.

The calculation of $C_m$ may also be used to detect misalignment of the inlet cannula; by providing a measure of muscle proximity to the cannula tip.

Electrode Design

A separate pair of electrodes is usually used for constant current excitation, and one or more pairs of electrodes are used to measure the conductance-dependent voltage. The reason for separate excitation electrodes is that the current density associated with excitation causes a polarization potential, which adds to the desired voltage measurement due to volume conductance. By separating excitation from sensing, the signal-to-noise ratio and signal stability are improved, at the expense of an additional pair of excitation electrodes.

Figure 2:
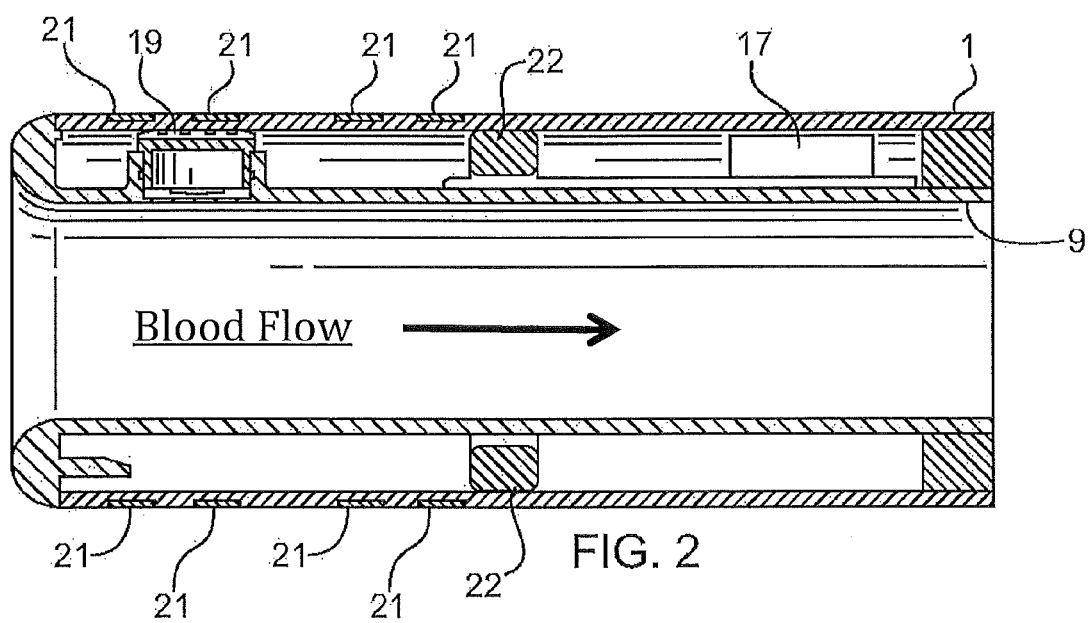
FIG. 2 shows an inlet cannula with integrated pressure and volume sensors. Data may be transmitted wirelessly to the VAD controller, which may be external or internal.

As shown in the embodiment of FIG. 2, the cannula may be built with tetrapolar ring electrodes, using four platinum or platinum-iridium ring electrodes, installed into grooves on a PEEK cannula body. Signals recorded from the smart tip conductance sensor during an acute ovine study are shown in FIGS. 9 and 10. The conductance measurement is shown compared to the ventricular short axis dimension obtained using sonomicrometry. Conductance increases/decreases as the LV axis dimension increases/decreases. FIG. 2 shows an outer wall 1, inner wall 9, pressure sensor 19, conductance electrode 21, and electronics suite 17. A RF coil 22 is also shown. Blood flow direction is also shown in FIG. 2.

Further embodiments may eliminate the two inner electrodes by using the outer electrodes as combined excitation and sensing electrodes. The effect of the polarization potential can be reduced by using higher excitation frequency, and lower current density.

Historicallly, there has been an increase in excitation frequency from tens of kHz to 100 kHz. In a typical smart cannula application according to an embodiment of the invention, the electrode surface area is significantly higher than in conventional conductance catheters. One embodiment uses a user defined excitation frequency that can vary between 1 and 100 kHz.

Typical values for excitation current in conventional conductance electrodes are in the microamp range. Low current density is desired to minimize the effect of the polarization potential, due to limited ion mobility at the electrode-tissue interface. In the current embodiment, the larger surface area electrodes allow increased excitation currents to be used (e.g. 0.5 to 5 mA) used while maintaining low current density. The increased excitation current improves the signal to noise ratio in the recorded signal.

The excitation frequency, magnitude, and bipolar/tetrapolar arrangement may be selectable through telemetry, and software controlled in the cannula. In various embodiments it will be possible to rapidly switch these modes, even during a cardiac cycle, to compare the effect of bipolar vs tetrapolar, excitation frequency, and excitation current magnitude.

Electronics, Power, Telemetry

One option to access the pressure sensor and conductance catheter would be by direct wiring, ie. a miniature cable from the cannula to the VAD controller. However, implantable electronics, with wireless telemetry of the pressure and volume signals, offers a number of advantages in terms of development and staged integration with VAD controllers.

Advantages may include, for example improved ease of integration with existing controllers without necessitating an additional percutaneous line.

System Architecture

FIG. 5 shows an implanted portion of one embodiment of the smart cannula electronics. Because of the current level of miniaturization in surface mount packaging, driven by the market for portable electronics (cell phones, iPods, laptops, etc.) embodiments may be created without the use of custom ICs. One may use custom and semi-custom options, such as ASICs, which can integrate most of the functions on a single chip.

Power

In one embodiment, an LVAD of an embodiment of the invention is powered as follows:

Class E transceiver 1-2 MHz parallel tuned secondary

Highest load requirements ~10 mA, 3.3.V, 330 mW.

Outgoing Telemetry

In one embodiment, useful outgoing telemetry transmitted by the LVAD includes the following:

Baseband data: serial, 3 channels (Pressure, Conductance mag, Conductance phase) 100 samples/sec each=300 samples/sec 12 bits per sample=3600 bits/sec Outgoing—impedance modulation at 2 FSK frequencies centered at a minimum of ~10 times bit rate=36000 Hz; e.g. FSK frequencies of 40 kHz and 60 kHz Detection by tracking frequency changes in Class E driver. Need FSK because frequency will shift with coupling etc. Class E controller needs to be fast enough to track 40-60 kHz, or track slowly and detect the phase error, as long as the error is small and does not impact efficiency or EMI.

Ingoing Telemetry

In embodiments of the invention, inbound telemetry received by an LVAD may include the following Baseband data: very slow (e.g. 10 bits/sec), used to select bipolar/tetrapolar, and excitation magnitude and frequency.

ASK may be obtained by modulating the Class E drive magnitude at ASK frequency of 0 Hz and 100 Hz; detected at implant by simple peak detector, demodulate in implant software using timer.

External Transceiver

External transceiver functions are shown in FIG. 6.

Sensor Scaling and Correction

The pressure sensor may include coefficients for one or both of pressure and temperature compensation, which will be calculated by an internal microprocessor.

Barometric pressure will be measured externally, using the same sensor family as used internally, and the barometric pressure will be subtracted from the absolute pressure measure from the smart cannula.

LVAD Speed Calculation

Suction Avoidance

Using the inlet conductance catheter an algorithm has been developed to control the pump speed of continuous flow LVADs. There are two aims of the control system: (1) immediate speed reduction following detection of suction, and (2) beat-to-beat control of pump speed based on end diastolic volume (EDV).

LV volume will be continuously monitored to detection suction. Suction can occur if the pump speed is too high or there is insufficient blood flow return to the LV. A threshold value will be set empirically, and a drop in LV volume below the threshold level will trigger an immediate reduction in pump speed until the suction event is resolved.

Suction detection using the smart tip conductance electrodes during and acute ovine study is shown in FIG. 10. Conductance recordings over 1 cardiac cycle are shown as speed increased from 7000 to 11700 rpm. At 11400 rpm suction occurred as can be seen as a reduction in the magnitude and pulsatility of the conductance signal. The LV short axis measured using sonomicrometry was used as a reference for the study.

A suction detection algorithm has been developed using inlet pressure. Suction is readily detectable as a highly negative, short duration signal (i.e. large −dP/dt) from the pressure sensor. Smaller amplitude negative pressure transients occur at the beats leading up to complete suction. An example of suction detection in an acute calf study is shown in FIG. 11. Pump speed was increased until suction was detected by dP/dt exceeding a pre-determined threshold. Following suction detection, pump speed was automatically reduced and the suction event was eliminated. After resolution of suction, pump speed was gradually increased to the set point. The control system was able to detect suction events and reduce pump speed immediately to resolve the suction event.

LV Unloading Control

In the absence of suction events the control system will adjust pump speed to optimize pump flow and reduce LV pressure and volume loading. Unloading will be set by measuring the end diastolic volume (EDV) on a beat-to-beat basis and adjusting the pump speed accordingly as depicted in FIG. 7. An increase in EDV with activity, etc. will cause an appropriate increase in pump speed to provide more unloading and circulatory support. A decrease in EDV may occur during rest or sleep, and the pump will reduce speed accordingly to prevent suction. It is expected that the initial EDV set point, and a EDV set point range, will be determined for a given patient based on echocardiographic assessment of LV volume and the frequency of aortic valve opening. Weaker hearts will tend to have lower EDV set points. As compared to current fixed speed pump control system, the proposed control system will provide pump flow that adapts to physiologic demand.

In addition to using EDV to adjust pump speed, we have developed a control system to adjust speed based on either LV end-diastolic pressure (EDP) or peak-to-peak pressure (Pppk) to assess cardiac preload. Pppk is defined as the difference between the end-systolic and end-diastolic pressures over each cardiac cycle. Using this relative pressure measurement mediates the possibility of baseline drift of the pressure sensor signal. The control system was tested in an acute sheep study, and the results are shown in FIG. 12. Initially, the control system set the pump speed to 8000 rpm. Partial occlusion of the IVC reduced LV EDP and Pppk, and the control system responded by decreasing pump support. The system stabilized at a reduced pump speed and LV EDP and Pppk returned to baseline. The occlusion was then released causing an increase in LV EDP and Pppk, and the control system responded by increasing pump support.

Long Term Management of LV Conditioning—Assessing Contractility from Direct Measurement of Pressure-Volume Relationship Evaluation of ventricular function is essential to determine myocardial recovery and weaning from pump support. End-systolic elastance ($E_{es}$) and the end-diastolic pressure volume relationship (EDPVR) are the gold standards for assessing native heart systolic and diastolic function, respectively (Suga and Sagawa 1974). Indirect assessment techniques of systolic function have been developed due to the inability to measure the pressure-volume relationship directly (Endo, Araki et al. 2001; Kikugawa 2001; Nakata, Shiono et al. 2001; Naiyanetr, Moscato et al. 2009). These methods rely on current or flow measurements and the inverse calculation of ventricular pressure and volume that requires multiple assumptions. In addition, these techniques are not able to assess diastolic function. With the proposed cannula the pressure-volume relationship of the native ventricle will be measured directly, which will enable the use of $E_{es}$ and EDPVR to assess ventricular function.

Traditional measurement of $E_{es}$ and EDPVR require venal occlusion to generate serial pressure-volume loops. To enable non-invasive measurements, Sensaki et al. and Shishido et al. developed single-beat methods to assess $E_{es}$ without the need for serial pressure-volume data. The methods use a normalized elastance function that is fit to the single pressure-volume loop during the isovolumetric contraction and ejection phases. Sensaki et al. reported the single-beat method as one that provides a reliable estimate of contractility in humans that is minimally affected by loading conditions. The method has been shown capable of estimating native contractility even during assistance with rotary blood pumps. Recently, a similar single-beat method has been reported to estimate EDPVR (Klotz, Hay et al. 2006). Single-beat estimation of $E_{es}$ and EDPVR has been proven in heart failure patients to be an effective clinical tool.

Using a single-beat method, $E_{es}$ and EDPVR are obtained periodically from the pressure-volume loop data. A baseline systolic and diastolic function level are determined for each patient at initial pump support, and improvement in systolic and diastolic function are determined relative to the baseline level. To minimize variability due to pump support, the pump speed will be fixed during baseline evaluation and all subsequent functional assessments. Absolute functional levels are not required to assess functional recovery, and therefore, errors in the single-beat method will be mitigated. By providing a real-time estimate of myocardial functional improvement, clinicians will be able to evaluate and optimize unloading strategies in order to enhance recovery and device weaning.

Physical Integration of the Smart Cannula into Existing or Future LVADs

To integrate the smart cannula with existing LVADs the physical dimensions of the device would have to change but the basic design would not be affected. Physical integration of one embodiment of a smart cannula into existing or future LVADs is straightforward.

Any documents referenced above are incorporated by reference herein. Their inclusion is not an admission that they are material or that they are otherwise prior art for any purpose.

We claim:

1. A method for adjusting flow of blood through a left ventricular assist device, comprising:
   determining at least one of ventricular pressure, ventricular volume, and ventricular wall location using a tip for attachment to a left ventricular assist device, wherein:
   the tip comprises an inner wall and an outer wall having a distance between them defining a cavity;
   said inner wall further defines a passage for movement of blood there through;
   at least one conductance sensor is disposed about the outer wall;
   at least one pressure sensor is disposed in the cavity; and
   said tip is in communication with a control system; and adjusting blood flow through a left ventricular assist device including said cannula, wherein said blood flow is adjusted to maintain end-diastolic volume or end-diastolic pressure;

wherein ventricular volume is determined, and wherein ventricular volume is determined using the equation:

$$V = \frac{1}{\alpha} \times \rho \times L^2 \times (G - G^p).$$

2. The method of claim 1, wherein ventricular volume is determined, and wherein ventricular volume is determined using the equation:

$$\text{Volume} = \frac{1}{1 - G_b/\gamma} \rho L^2 (G_b).$$

3. The method of claim 1, wherein said blood flow is adjusted to minimize occurrences of negative pressure.

4. The method of claim 1, wherein said at least one conductance sensor comprises a series of electrodes.

5. The method of claim 4, wherein the series of electrodes have a shape selected from the group consisting of ring-shaped and patch-shaped.

6. The method of claim 1, further comprising placing said tip in communication with a radio frequency power supply for operation of the left ventricular assist device.

7. A method for adjusting flow of blood through a left ventricular assist device, comprising:
   determining at least one of ventricular pressure, ventricular volume, and ventricular wall location using a tip for attachment to a left ventricular assist device, wherein:
      the tip comprises an inner wall and an outer wall having a distance between them defining a cavity;
      said inner wall further defines a passage for movement of blood there through;
      at least one conductance sensor is disposed about the outer wall;
      at least one pressure sensor is disposed in the cavity; and
      said tip is in communication with a control system;
   generating an isolation diaphragm to prevent the pressure sensor from having direct contact with said blood; and
   adjusting blood flow through a left ventricular assist device including said cannula, wherein said blood flow is adjusted to maintain end-diastolic volume or end-diastolic pressure;
   wherein ventricular volume is determined, and wherein ventricular volume is determined using the equation:

$$V = \frac{1}{\alpha} \times \rho \times L^2 \times (G - G^p).$$

8. The method of claim 7, wherein generating the isolation diaphragm further comprises coupling the pressure sensor to the cavity via incompressible gel or silicon oil.

9. The method of claim 7, wherein ventricular volume is determined, and wherein ventricular volume is determined using the equation:

$$\text{Volume} = \frac{1}{1 - G_b/\gamma} \rho L^2 (G_b).$$

10. The method of claim 7, wherein said blood flow is adjusted to minimize occurrences of negative pressure.

11. The method of claim 7, wherein said at least one conductance sensor comprises a series of electrodes.

12. The method of claim 11, wherein the series of electrodes have a shape selected from the group consisting of ring-shaped and patch-shaped.

13. The method of claim 7, further comprising placing said tip in communication with a radio frequency power supply for operation of the left ventricular assist device.

14. A method for adjusting flow of blood through a left ventricular assist device, comprising:
   determining at least one of ventricular pressure, ventricular volume, and ventricular wall location using a tip for attachment to a left ventricular assist device, wherein:
      the tip comprises an inner wall, an outer wall, and an apical region, the inner wall and the outer wall having a distance between them defining a cavity;
      said inner wall further defines a passage for movement of blood there through;
      at least one conductance sensor is disposed about the outer wall, said at least one conductance sensor comprises at least one electrode;
      at least one pressure sensor is disposed in the cavity; and
      said tip is in communication with a control system;
   generating a configuration for the at least one electrode so as to only be sensitive to blood volume near the tip; and
   adjusting blood flow through a left ventricular assist device including said cannula, wherein said blood flow is adjusted to maintain end-diastolic volume or end-diastolic pressure;
   wherein ventricular volume is determined, and wherein ventricular volume is determined using the equation:

$$V = \frac{1}{\alpha} \times \rho \times L^2 \times (G - G^p).$$

15. The method of claim 14, wherein ventricular volume is determined, and wherein ventricular volume is determined using the equation:

$$\text{Volume} = \frac{1}{1 - G_b/\gamma} \rho L^2 (G_b).$$

16. The method of claim 14, wherein said blood flow is adjusted to minimize occurrences of negative pressure.

17. The method of claim 14, further comprising placing said tip in communication with a radio frequency power supply for operation of the left ventricular assist device.

18. The method of claim 14, wherein said at least one conductance sensor comprises a series of electrodes.

19. The method of claim 18, wherein the series of electrodes have a shape selected from the group consisting of ring-shaped and patch-shaped.

20. The method of claim 18, further comprising generating an isolation diaphragm to prevent the pressure sensor from having direct contact with said blood.

* * * * *